United States Patent
Edvinsson et al.

(10) Patent No.: US 9,273,351 B2
(45) Date of Patent: Mar. 1, 2016

(54) DEVICE AND METHOD FOR CONDUCTING DIRECT QUANTITATIVE REAL TIME PCR

(75) Inventors: Lars Edvinsson, Uppsala (SE); Magnus Molin, Uppsala (SE)

(73) Assignee: AlphaHelix Molecular Diagnostics AB, Umea (SE)

( * ) Notice: Subject to any disclaimer, the term of this patent is extended or adjusted under 35 U.S.C. 154(b) by 180 days.

(21) Appl. No.: 13/817,899

(22) PCT Filed: Sep. 24, 2010

(86) PCT No.: PCT/EP2010/064096
§ 371 (c)(1),
(2), (4) Date: Feb. 20, 2013

(87) PCT Pub. No.: WO2012/037978
PCT Pub. Date: Mar. 29, 2012

(65) Prior Publication Data
US 2013/0157276 A1    Jun. 20, 2013

(51) Int. Cl.
*C12Q 1/68* (2006.01)
*C12P 19/34* (2006.01)
*B01L 7/00* (2006.01)
*G01N 21/07* (2006.01)
*G01N 21/64* (2006.01)
*G01N 21/51* (2006.01)

(52) U.S. Cl.
CPC . *C12Q 1/686* (2013.01); *B01L 7/52* (2013.01); *B01L 7/525* (2013.01); *G01N 21/07* (2013.01); *G01N 21/6452* (2013.01); *B01L 2200/10* (2013.01); *B01L 2200/14* (2013.01); *B01L 2300/0654* (2013.01); *B01L 2400/0409* (2013.01); *G01N 2021/513* (2013.01); *G01N 2021/6491* (2013.01)

(58) Field of Classification Search
CPC .............. B01L 7/00; B01L 7/52; B01L 7/525; B01L 7/5255; B01L 2300/0803; B01L 2300/0654; B01L 2400/04; B01L 2400/0403; B01L 2400/0409; C12Q 1/686
See application file for complete search history.

(56) References Cited

U.S. PATENT DOCUMENTS

2002/0177144 A1 * 11/2002 Remacle et al. ................. 435/6

FOREIGN PATENT DOCUMENTS

| WO | 98/49340 | 11/1998 |
|----|----------|---------|
| WO | 00/58013 | 10/2000 |
| WO | 03/102226 | 12/2003 |
| WO | 2005045075 | 5/2005 |

OTHER PUBLICATIONS

International Search Report from corresponding International Application No. PCT/EP2010/064096, mailed on Jun. 30, 2011.

* cited by examiner

*Primary Examiner* — Young J Kim
(74) *Attorney, Agent, or Firm* — Renner, Otto, Boisselle and Sklar, LLP

(57) ABSTRACT

A method and device for performing direct quantitative real time PCR in a crude sample (200), wherein said sample is subjected to a centrifugal force sufficient to separate components of the sample into a supernatant and a pellet, and wherein at least one light source (204) and at least one detector (205) are positioned so that the excitation light impinges on the sample in a position above said pellet, and said detector detects light emitted from a position above said pellet.

3 Claims, 4 Drawing Sheets

DEVICE AND METHOD FOR CONDUCTING DIRECT QUANTITATIVE REAL TIME PCR

TECHNICAL FIELD

The present invention relates the field of molecular biology, methods and devices for conducting DNA amplification, and in particular to a method and device for conducting direct real time quantitative PCR (qPCR).

BACKGROUND

Polymerase chain reaction (PCR) was developed in the 1980s and is today the most commonly used method for amplifying DNA and has become a central tool in both synthesis and analysis of DNA in a multitude of applications.

In traditional PCR amplification, the sample or source material is pretreated in order to extract and purify DNA. It is also desirable to remove or neutralize various PCR inhibitors present in the sample or source material, as it is well known that wild-type Taq polymerase is easily inhibited by cellular debris.

Newly developed more robust polymerase enzymes have however made it possible to amplify DNA directly from a crude or minimally treated sample or source material. This approach has been coined "direct PCR". Direct PCR has great potential for use in various diagnostic applications, where a simplified sample handling and faster turnaround times from sampling to results would give significant benefits to both the user and the patients.

While potentially offering savings in time and cost, quantitative direct PCR also has some problems to overcome before it can be used in diagnostic and environmental applications, where the typical samples such as saliva, buccal swabs, tissue samples, blood, cell culture, plant material, soil samples etc often contain a complex mixture of organic and inorganic debris.

The general procedure for performing direct PCR on complex samples usually involves an initial denaturation to release DNA for amplification. It is suggested that the results can be improved by performing the denaturation in a suitable buffer, spinning down the cellular debris and using the cleared supernatant in the PCR. This however requires an additional step of collecting the supernatant and transferring it to a system for performing the PCR.

When direct PCR is performed in a heating block, the central element of all conventional PCR instruments, real time quantitative PCR (qPCR) requires that excitation light is directed into the sample container, and emitted light read from the same direction. Frequently this is done from above, as only the opening of the container is available, when the remaining container is surrounded by the heating block. In a crude sample, the fluorescence is attenuated and scattered by particulate matter, such as cell debris, present in the sample. Further, reflected excitation light may interfere with the reading of the emission light, and filter arrangements may be necessary to eliminate reflected excitation light.

FIG. 1, panel A, schematically illustrates the above described background art, showing a PCR tube 101 containing a sample 102 placed in a heating block 103. A light source 104 and a detector 105 are positioned above the opening of the PCR tube.

There are only a few automated, rotary systems, such as the Rotor Gene® (formerly Corbett Life Sciences Inc., now Qiagen Inc.) or the QuanTyper™-48 instrument (AlphaHelix Molecular Diagnostics AB), capable of performing qPCR. In these, excitation light is emitted by a light source positioned substantially at a right angle to the sample container, and emission light is detected by a sensor positioned at the apices of the container, detecting light emitted along the longitudinal axis of the containers. The rounded bottom or apice of the sample containers, frequently commercially available PCR-tubes, is used as a lens, collecting the emission light.

FIG. 1, panel B, schematically illustrates the above described background art, showing a PCR tube 101 containing a sample 102 placed in a rotor 110. A light source 104 and a detector 105 are arranged outside the rotational path of the PCR-tubes.

When qPCR is performed on a crude sample, the complex nature of the sample influences the sensitivity, reliability and repeatability of the result, in particular because of difficulties in the excitation, reading and quantification of the fluorescence.

WO 00/58013 discloses a device for performing PCR, where a significant centrifugal force is utilized to homogenize the sample with respect to temperature. The efficient homogenization makes it possible to heat the samples more aggressively, without risking over-shooting, and the uninterrupted centrifugation makes it possible to rapidly cool the samples. The result is significantly shortened ramping-times, thus minimizing the time required for performing PCR. The disclosure mentions the possibility of using a radiation source and a reflectance sensor for detecting chemical reactions in the samples, e.g. the light reflectance or emission indicating the end point of a reaction or a positive or negative test answer. The disclosure however does not address the issues of direct PCR.

GB 1 402 225 concerns a rotary dynamic multi-station photometer-fluorometer. It is suggested that the most obvious arrangement is that where a light source is disposed on one side of a sample-holding cuvette and a photodetector on the other, but that such arrangement requires appropriate filters in order to eliminate the excitation light passing through the sample. The elimination of interfering excitation light may also be accomplished by angled excitation emission detection wherein the excitation beam is oriented 90 degrees with respect to the photodetector which measures the emitted fluorescence.

GB 1 402 225 also mention another problem associated with determining solute concentration by fluorescence measurement, which occurs where the sample is characterized by relatively high absorbance. In practice, the sample itself attenuates the excitation, and this phenomenon is often referred to as the "inner filter effect".

When performing quantitative direct PCR, handling the complex sample poses problems that existing methods and devices are not well equipped to handle. There is a need of improvements in the methods and devices for performing quantitative direct PCR in order to achieve repeatable and reliable results, in particular when performing qPCR on crude samples such as, but not limited to, saliva, buccal swabs, tissue samples, blood, cell culture, plant material, soil samples etc, which often contain a complex mixture of organic and inorganic debris. For diagnostic purposes, there is a need for improvements in the handling and analysis of in particular whole blood samples.

SUMMARY

An object of the present invention is to address the problems associated with performing qPCR on crude samples or minimally treated samples, and to make available a method and device allowing reliable and repeatable qPCR analysis of crude samples or minimally treated samples. This and other objects that become evident to a skilled person upon study of the present description and examples, are realized by a device and method as defined in the attached claims, incorporated herein by reference.

One embodiment of the invention is a device for performing direct quantitative real time PCR, said device comprising a rotor for receiving one or more elongate containers having an opening for receiving one or more samples, a distal end, and a longitudinal axis, rotating said containers along a circular path and subjecting said samples in said containers to a centrifugal force, at least one light source for subjecting the sample to excitation light, and at least one detector for detecting light emitted from the sample, wherein said rotor holds said elongate containers in a position where the longitudinal axis of each container is parallel to the radius of said rotor; at least one light source and said at least one detector are positioned in relation to the rotor so that the excitation light impinges on the container in a position between the distal end of the container and the opening of the container, and said detector detects light emitted from the sample from a position between the distal end of the container and the opening of the container.

Another embodiment is a method for performing direct quantitative real time PCR on a sample comprising the steps of placing said sample in an elongate container; subjecting said sample in said container to a centrifugal force; subjecting the sample to excitation light from a light source; and detecting light emitted from the sample using a detector; wherein said elongate containers are subjected to a centrifugal force in a rotor which holds the containers in a position where the longitudinal axis of each container is parallel to the radius of said rotor; wherein at least one light source and said at least one detector are positioned in relation to the rotor so that the excitation light impinges on the container in a position between the distal end of the container and the opening of the container, and said detector detects light emitted from the sample from a position between the distal end of the container and the opening of the container.

Further embodiments of the device and method are disclosed in the description and attached claims, incorporated herein by reference.

BRIEF DESCRIPTION OF DRAWINGS

The invention is now described, by way of example, with reference to the accompanying drawings, in which.

DESCRIPTION OF EMBODIMENTS

Figure 1A:
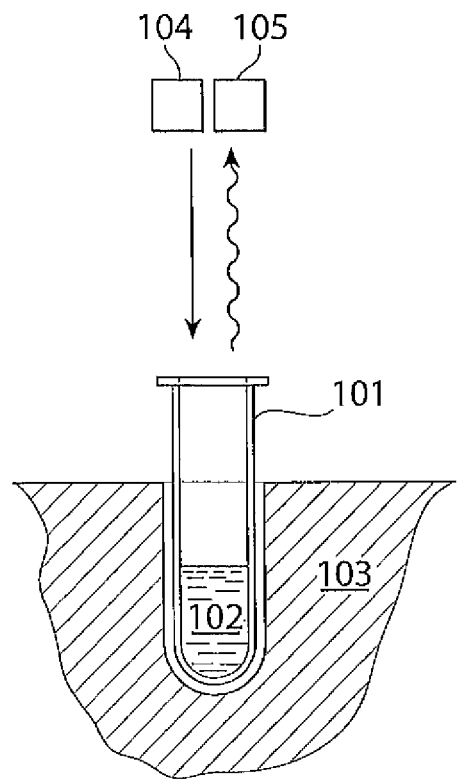
FIG. 1 schematically shows the fluorescence reading in (A) a conventional stationary PCR instrument, and (B) in a rotary PCR instrument.
Figure 1B:
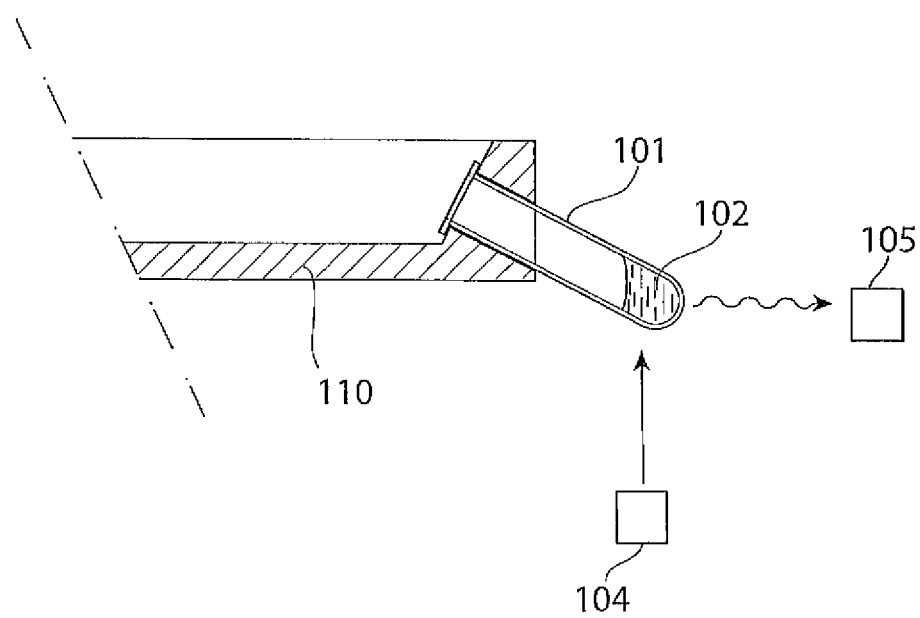

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In addition to the above, the following terms will be used:

The expression "crude sample" is intended to encompass samples subjected to analysis without or substantially without pre-treatment, such as sedimentation, filtration, extraction of DNA or with only very rudimental pre-treatment, such as the addition of heparin to a blood sample, the addition of buffer to a soil sample, coarse filtration etc.

The term "excitation light" is meant to encompass both visible and non-visible, e.g. ultraviolet radiation, used to bring molecules in a sample or in particular in a marker, present in the sample, to an excited state.

The term "emitted light" or "emission light" is meant to encompass both visible and non-visible radiation emitted by a susceptible molecule from an electronically excited state.

The term "pellet" is used to describe the accumulation of denser material, e.g. cellular debris, platelets etc, in the distal end of the container holding the sample, when subjected to centrifugation. Using the term "pellet" does not exclude the existence of a density gradient, i.e. a situation where there is no sharp interface between the sedimented portion of the sample, and a supernatant. The term "pellet" will in that case refer to a portion of said density gradient practically discernable based on its absorption properties.

In the following, a detailed description of different embodiments will be given. It should be noted that the embodiments and features thereof can be freely combined into embodiments not specifically disclosed, but falling under the general scope of the claims.

A first embodiment of the invention comprises a device for performing direct quantitative real time PCR, said device comprising a rotor for receiving one or more elongate containers having a proximal end with an opening for receiving one or more samples, a distal, closed end, and a longitudinal axis; said rotor rotating said containers along a circular path and subjecting said samples in said containers to a centrifugal force; at least one light source for subjecting the sample to excitation light, and at least one detector for detecting light emitted from the sample; wherein said rotor holds said elongate containers in a position where the longitudinal axis of each container is parallel to the radius of said rotor; at least one light source and said at least one detector are positioned in relation to the rotor so that the excitation light impinges on the container in a position between the distal end of the container and the opening of the container, and said detector detects light emitted from the sample from a position between the distal end of the container and the opening of the container.

In the above embodiment, the longitudinal axis of each container as well as the radius of said rotor, are preferably horizontal.

In the above embodiment, said centrifugal force is preferably sufficient to separate the components of the sample into a substantially clear supernatant and a pellet. According to a preferred embodiment of the invention, freely combinable with all other features of the invention, said centrifugal force is at least 5×g, preferably at least about 10×g, more preferably at least about 100×g. According to another embodiment of the invention, also freely combinable with all other features of the invention, said centrifugal force is at least about 1000×g, preferably at least about 2000×g, more preferably at least about 3000×g. An advantage of using high centrifugal force is that the pellet forms more rapidly, and there are likely to be less marked changes in absorption or diffusion in the sample, potentially influencing the fluorescence reading.

Figure 2A:
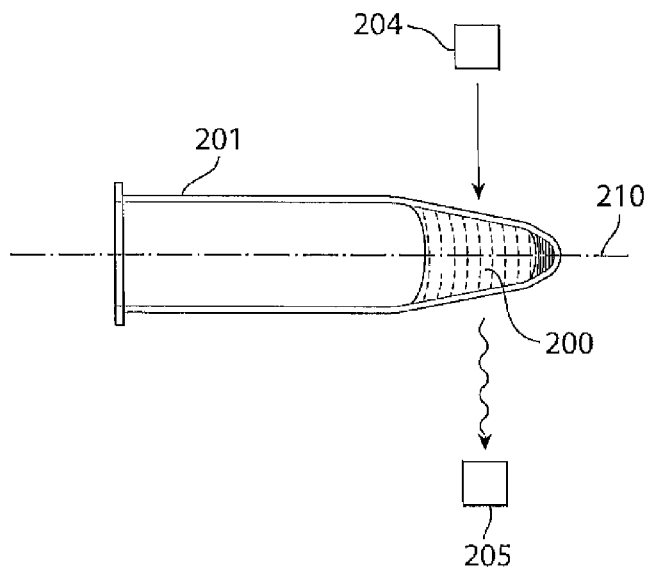
FIG. 2 schematically shows an embodiment where a device for emitting excitation light and a detector of emitted light are positioned on the opposite sides of a container holding a sample. Panel A is a longitudinal view, whereas Panel B is a transversal view.
Figure 2B:
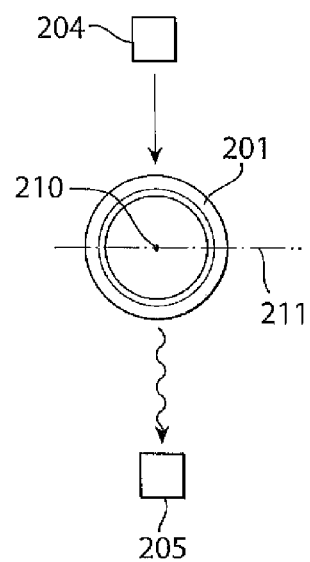

Further, said at least one light source and said at least one detector are preferably positioned in relation to the rotor so that the excitation light impinges on the container in a position above the pellet formed in the container, and said detector defects light emitted from the sample from a position above the pellet formed in the container. This embodiment is schematically illustrated in FIG. 2, Panel A, where a container 201, preferably a PCR-tube, is shown in horizontal position, as it would appear during centrifugation. A sample 200 is present in the distal end of the tube, and a pellet is indicated by a dashed area at distal end, i.e. the bottom of the tube. The longitudinal axis of the tube is indicated with the reference numeral 210, shown both in the longitudinal and transversal view.

A light source 204 is arranged on one side of the container or tube, and a detector 205 substantially on the opposite side. Panel B shows the same set up in a transversal view, where 210 indicates the longitudinal axis, and 211 indicates the plane of symmetry.

The light source and the detector are positioned in relation to the particular container and sample volume in such a fashion that the excitation light impinges on the container in a position above the pellet Formed in the container, and said detector detects light emitted from the sample from a position above the pellet formed in the container. However, preferably also the geometry of the container holding the sample is taken into account, so that excitation light impinges on the container in a position above the pellet formed in the container, and substantially in a 90 degree angle to the container wall. Similarly, said detector is preferably positioned to detect light emitted from the sample from a position above the pellet formed in the container, where the path from this position to the detector is substantially in a 90 degree angle to the container wall in the position where the emission light passes through the container wall.

Figure 3A:
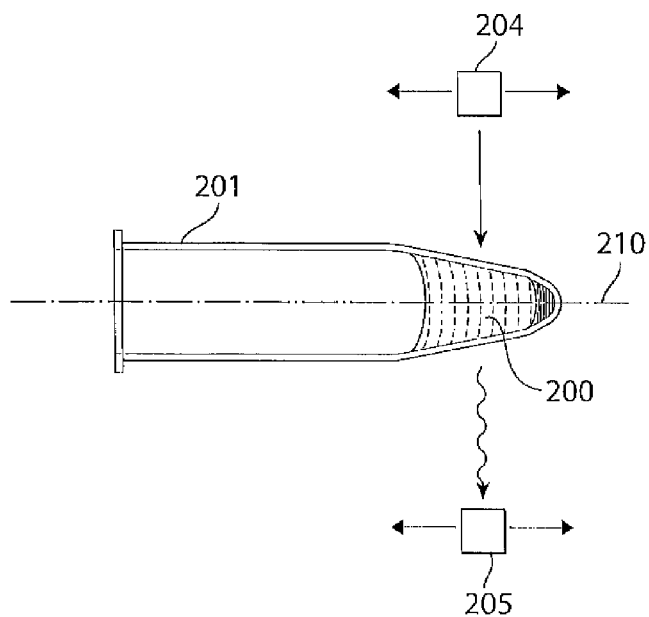
FIG. 3 schematically shows a preferred embodiment of the embodiment shown in FIG. 2, where one or both of a device for emitting excitation light and a detector of emitted light is/are movably positioned in relation to a container holding a sample. Panel A is a longitudinal view, whereas Panel B is a transversal view.
Figure 3B:
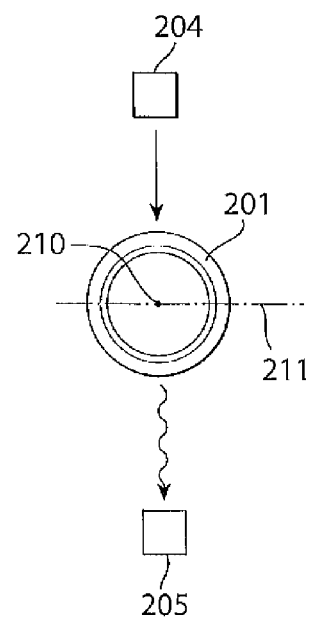

According to another embodiment, at least one of said light source and said detector is/are movably arranged in relation to the circular path taken by the elongate containers. In this embodiment, schematically shown in FIG. 3, Panels A and B, the light source 204, or the detector 205, or both, is/are movably arranged in relation to the container 201. Here each is schematically illustrated as being movable along an axis substantially parallel to the longitudinal axis 210 of the container 201. Panel B shows the same set up in a transversal view, where 210 indicates the longitudinal axis, and 211 indicates the plane of symmetry.

Again, the geometry of the container holding the sample is preferably taken into account, so that excitation light impinges on the container in a position above the pellet formed in the container, and substantially in a 90 degree angle to the container wall. Similarly, said detector is preferably positioned to detect light emitted from the sample from a position above the pellet formed in the container, where the path from this position to the detector is substantially in a 90 degree angle to the container wall in the position where the emission light passes through the container wall.

According to another embodiment (not shown), the light source 204, or the detector 205, or both, is/are adapted to be moved along an axis or path which is not parallel to the longitudinal axis 210. It is conceived that the light source 204, or the detector 205, or both, can be moved in parallel to the conical section of the container 201. Alternatively, in order to accommodate differently shaped containers, the light source 204, or the detector 205, or both, can be moved along a semi-circular or curved path, corresponding to the profile of the container holding the sample. Also here, the geometry of the container holding the sample is preferably taken into account, so that excitation light impinges on the container in a position above the pellet formed in the container, and substantially in a 90 degree angle to the container wall. Similarly, said detector is preferably positioned to detect light emitted From the sample from a position above the pellet formed in the container, where the path from this position to the detector is substantially in a 90 degree angle to the container wall in the position where the emission light passes through the container wall.

Figure 4A:
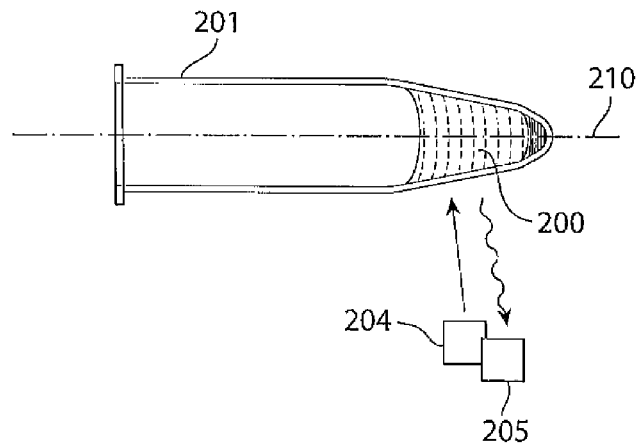
FIG. 4 schematically shows an embodiment where both the light source and the detector are positioned substantially on the same side of the plane of symmetry of a container holding a sample. Panel A is a longitudinal view, whereas Panel B is a transversal view.
Figure 4B:
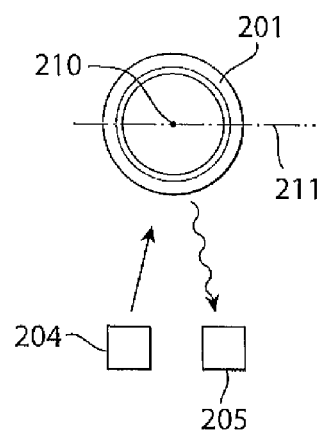

According to another embodiment, schematically shown in FIG. 4, both the light source 204 and the detector 205 are arranged on the same side of the plane of symmetry 211 as shown in Panel A and Panel B, where Panel A is a longitudinal view, and Panel B shows the same set up in a transversal view, where 210 indicates the longitudinal axis, and 211 indicates the plane of symmetry. Here, as indicated in the figure, the geometry of the container holding the sample is preferably taken into account, so that excitation light impinges on the container in a position above the pellet formed in the container, and substantially in a 90 degree angle to the container wall. Similarly, said detector is preferably positioned to detect light emitted from the sample from a position above the pellet formed in the container, where the path from this position to the detector is substantially in a 90 degree angle to the container wall in the position where the emission light passes through the container wall.

Figure 5A:
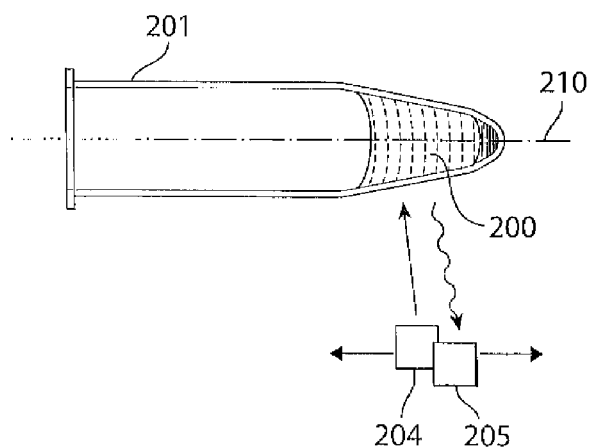
FIG. 5 shows a preferred embodiment of the embodiment shown in FIG. 4, where one or both of a device for emitting excitation light and a detector of emitted light is/are movably positioned in relation to a container holding a sample. Panel A is a longitudinal view, whereas Panel B is a transversal view.
Figure 5B:
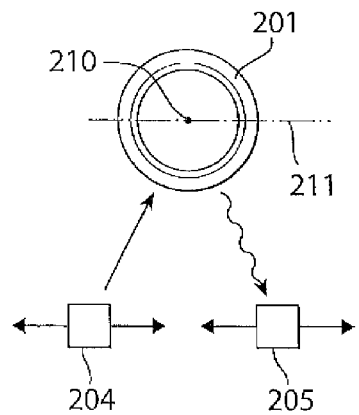

According to yet another embodiment, schematically shown in FIG. 5, both the light source 204 and the detector 205 are movable along the longitudinal axis 210, or as indicated in Panel B, movable in relation to each other, substantially along a segment of the rotational path of the containers 201 when the rotor is in operation. Preferably at least one of said light source and said detector is/are movably arranged to be moved along or parallel to the radius of the circular path taken by the containers.

The paths along which the light source and/or the detector is/are moved, indicated by arrows in FIGS. 5A and B, can also be tilted or curved, in order to conform to the geometry of the sample container. Preferably the geometry of the container holding the sample is taken into account, so that excitation light impinges on the container in a position above the pellet formed in the container, and substantially in a 90 degree angle to the container wall. Similarly, said detector is preferably positioned to detect light emitted from the sample from a position above the pellet formed in the container, where the path from this position to the detector is substantially in a 90 degree angle to the container wall in the position where the emission light passes through the container wall.

Figure 6:
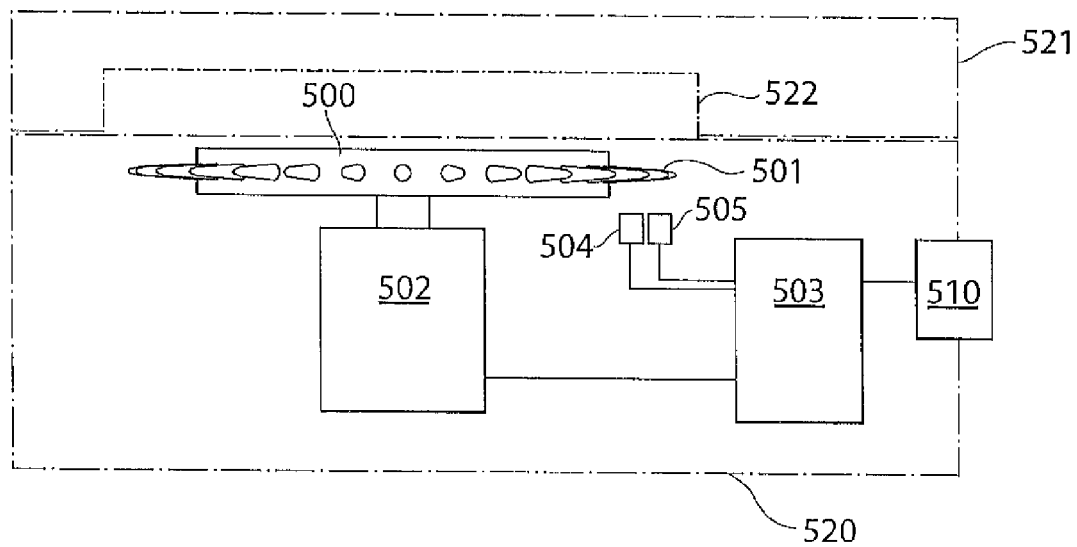
FIG. 6 schematically shows a schematic overview of a system according to an embodiment.

Another embodiment is a system as schematically illustrated in FIG. 6. Here a device as described in any one of, or all the embodiments above, comprises a motor 502 operatively connected to a rotor 500 for holding a number of containers 501, a light source 504, a detector 505, a control unit 503, and a user interface 510. In FIG. 6, the light source 504 and the detector 505 are shown as being both positioned below the rotor, but they can also be both positioned above the rotor, or positioned on each side of the rotor as indicated in FIGS. 2-5. Similarly, the light source 204 and the detector 205 can be movable to adjust the focus of the excitation light as well as the focus of the detector, the distance as well as the angle between light source and container wall, or detector and container wall.

The rotor 500 is adapted to hold a number of sample containers. Preferably said number of sample containers is a multiple of 12, such as 12, 24, 48 or 96. These containers for holding samples are for example test tubes, and in particular centrifuge tubes, preferably PCR tubes with individual hinged caps and thin side walls for efficient temperature transfer. Such tubes are commercially available from many different suppliers, such as Teklab Ltd., UK, or Eppendorf AG, Germany.

Suitable light sources 504 comprise but are not limited to lasers, photodiodes, and lamps, such as xenon arc lamps, mercury-vapor lamps and the like. A skilled person is capable of choosing the appropriate type of light source, and a skilled person also recognizes that some light sources emit light at specific wavelengths, whereas others emit broad spectral light. Consequently, a skilled person is capable of choosing an appropriate filter or monochromator or similar auxiliary equipment where and when needed.

Suitable detectors 505 comprise any photo detection device or photo sensor, for example but not limited to photomultiplier tubes (PMTs), photodiodes, charge-coupled devices (CCDs) etc. As above, a skilled person is capable of choosing a suitable detector and possible auxiliary equipment.

According to a preferred embodiment said device further comprises an outer cover 521 and an inner cover 522 wherein said inner cover 522 is adapted to be at least partially opened during operation of the rotor 500 without opening the outer cover 521.

The invention also makes available methods for performing direct quantitative real time PCR on a sample, preferably a method comprising the steps of
placing said sample in an elongate container,
subjecting said sample in said container to a centrifugal Force,
subjecting the sample to excitation light from a light source,
detecting light emitted from the sample using a detector,
wherein said elongate containers are subjected to a centrifugal force in a rotor which holds the containers in a position where the longitudinal axis of each container is parallel to the radius of said rotor; wherein at least one light source and said at least one detector are positioned in relation to the rotor so that the excitation light impinges on the container in a position between the distal end of the container and the opening of the container, and said detector detects light emitted from the sample from a position between the distal end of the container and the opening of the container.

In a method according to this embodiment, said sample is subjected to a centrifugal force sufficient to separate the components of the sample into a substantially clear supernatant and a pellet. According to a preferred embodiment of the method according to the invention, freely combinable with all other features of the invention, said centrifugal force is at least 5×g, preferably at least about 10×g, more preferably at least about 100×g. According to another embodiment of the method according to the invention, also freely combinable with all other features of the invention, said centrifugal force is at least about 1000×g, preferably at least about 2000×g, more preferably at least about 3000×g.

Further in a method according to any one of the embodiments, said at least one light source and said at least one detector are positioned in relation to the rotor so that the excitation light impinges on the container in a position above the pellet formed in the container, and said detector detects light emitted from the sample from a position above the pellet formed in the container.

As disclosed in relation to the device, the geometry of the container holding the sample is taken into account also in a method according to the invention, so that excitation light impinges on the container in a position above the pellet formed in the container, and substantially in a 90 degree angle to the container wall. Similarly, said detector is preferably positioned to detect light emitted from the sample from a position above the pellet formed in the container, where the path from this position to the detector is substantially in a 90 degree angle to the container wall in the position where the emission light passes through the container wall.

Preferably the method involves a step of detecting the interface between the pellet and the supernatant, and moving said at least one light source and/or said at least one detector in relation to the rotor so that the excitation light impinges on the container in a position above the pellet formed in the container, and said detector detects light emitted from the sample from a position above the pellet formed in the container. Alternatively, at least one of said light source and said detector is/are moved in relation to the circular path taken by the elongate containers. Alternatively, at least one of said light source and said detector is/are movably arranged to be moved along or parallel to the radius of the circular path taken by the containers.

According to another embodiment of the method, the amplification by thermocycling and consequently also the fluorescence reading, commences after formation of the pellet.

Preferably a method according to the invention involves the step of measuring the absorbance of the sample, preferably in the supernatant, intermittently or continuously, wherein a measured change in absorbance is used to reduce and compensate for the influence of absorption on the fluorescence.

Alternatively, or in combination with the above embodiment, the invention involves the step of measuring the diffusion and/or reflectance of the sample, preferably in the supernatant, intermittently or continuously, wherein a measured change in diffusion and/or reflectance is used to reduce and compensate for the influence of absorption on the fluorescence.

An embodiment of the method according to the invention may comprise the following steps:
addition of reagents to a sample,
subjecting a sample to centrifugation >5×g, preferably at least about 10×g, more preferably at least about 100×g, or at least about 1000×g, preferably at least about 2000× g, more preferably at least about 3000×g
measuring the absorbance of the sample, preferably the supernatant formed during centrifugation performing cyclic amplification detecting an increasing fluorescence signal in at least one sample and/or in a positive control, in the absence of a fluorescence signal from said positive control, issue an error message, or displaying the results of the amplification.

In the above method, a positive control can be either a positive internal control, or a positive external control. When a fluorescence signal is detected from the control, but not from the samples, this indicates that the analysis result is negative, i.e. the sequence to be amplified was not present in the sample.

The sample can be subjected to centrifugation before, after or simultaneously with the addition of the PCR reagents, e.g. polymerases, buffers, transcriptases, nucleotides etc. It is contemplated that the reagents are added to the sample before centrifugation, and the reagents mixed with the sample. However, in cases where a crude sample is suspected of containing interfering components that may desaturate or otherwise negatively influence the PCR reagents, an initial centrifugation is preferably performed before the addition of the reagents, in order to separate such interfering components from the bulk of the sample.

The advantages of the embodiments of the present invention will become evident to persons skilled in the art upon a closer study of the present description, examples, claims and drawings.

It is for example a significant advantage to be able to perform real time qualitative direct PCR on samples containing particulate matter, such as cells and cell debris, without an attenuation of the fluorescence.

It is also an advantage to be able to adjust the position at which the emitted light is detected, as made possible by certain embodiments of the invention, or combinations of embodiments. This makes it possible to individualize the analysis of different types of samples, accounting for differences in sample volume, pellet volume etc.

The feature of the containers being rotated in a position where the longitudinal axis of each container is parallel to the radius of said rotor has inter alia the advantage that the pellet is formed substantially symmetrically in the bottom of the sample container. This reduced the influence of the pellet, its properties, such as the size of the pellet, and allows accurate and repeatable fluorescence reading. A uniform and repeatable localization of the pellet simplifies the reading, in particular the correct positioning of the light source and detector, which in turn reduces or removes disturbing factors detrimental to the accuracy and repeatability of the analysis.

The feature of measuring the absorbance and/or diffusion of the sample either continuously or intermittently gives a significant, additional advantage in that artifacts due to changing sample absorption and/or diffusion can be greatly reduced.

The feature of detecting emitted light emanating from the supernatant and passing through the side wall of the sample container has the advantage of avoiding the attenuation of the signal caused by the pellet. Further, as there are PCR tubes having different shapes in particular with regard to their distal end, for example flat, conical or round bottom, possible variations caused by different tube geometry can now be avoided.

EXAMPLES

Example 1

Increasing Concentration of Blood Prevents Performance of Real Time PCR

Whole blood is a good example of complex samples, where both biochemical and physical components may interfere with the analysis. Needless to say, blood is an important sample in diagnostic and forensic PCR analysis. The presence of whole blood in a sample, or using whole blood as the sample, is known to restrict the performance of real time PCR analysis.

In experiments where increasing amounts of blood have been added to a sample, the results indicate that the number of cycles required for the fluorescent signal to exceed background level (the cycle threshold, or Ct value) increase with increasing concentration of blood in the sample. Depending on the equipment used for performing the PCR, the practical limit is about 10 to about 25% blood.

Example 2

Centrifugation Helps to Eliminate the Interference of Whole Blood

In a series of experiments, the inventors subjected the samples to centrifugation forming a pellet. The samples containing different amounts of blood were subjected to about 3000×g in a commercially available instrument, the Quan-Typer-48™ (AlphaHelix Molecular Diagnostics AB, Uppsala, Sweden). The results show that increasing concentrations of blood were accompanied by an increase in Ct values, but that the PCR-reaction itself continued unhindered.

The results indicate that centrifugation at high g-force led to the formation of a pellet, and that the attenuation of excitation light was reduced. However, in a conventional apparatus, the emitted fluorescence is attenuated by the pellet, and at a blood concentration of 23%, the attenuation was practically unacceptable.

It is contemplated that—depending on the centrifugal force—a blood concentration up to about 50%, preferably up to about 60% or higher, for example up to about 80%, about 90% or about 100% can be handled. Further, an addition of reagents, such as suitable buffers and enzymes, will always be necessary before performing PCR amplification, and that the concentration of blood would therefore in practice always be less than about 100%.

It should however not be ruled out that the centrifugation and formation of a pellet is performed before or simultaneously with the addition of reagents. Considering this, one embodiment of the invention encompasses a situation where the sample is whole blood, and where thus the concentration of blood is about 100 or exactly 100% at the starting point.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. A method for performing direct quantitative real time PCR on a sample, comprising:

placing said sample for amplification in an elongate container having an opening and a distal end, subjecting said sample in said container to a centrifugal force sufficient to separate components of the sample into a supernatant and a pellet, amplifying nucleic acids in the supernatant, subjecting the sample to excitation light from a light source, detecting light emitted from the sample using a detector, displaying results of the amplification based on the detected light emitted from the sample, wherein said elongate container is subjected to a centrifugal force in a rotor which holds said container in a position where the longitudinal axis of the container is parallel to the radius of said rotor; wherein said light source and said detector are movably arranged in relation to the rotor so that the excitation light impinges on the container in a position between said distal end of the container and the opening of the container, and said detector detects light emitted from the sample from a position between said distal end of the container and the opening of the container, and wherein an interface between the pellet and the supernatant is detected, and said light source and/or said detector are moved in relation to the rotor so that the excitation light impinges on the container in a position above the pellet formed in the container, and said detector detects light emitted from the sample from a position above the pellet formed in the container.

2. The method according to claim 1, wherein at least one of said light source and said detector is/are moved in relation to the circular path taken by the elongate container.

3. The method according to claim 1, wherein at least one of said light source and said detector is/are movably arranged to be moved along or parallel to the radius of the circular path taken by the container.

* * * * *